United States Patent
Craig et al.

(10) Patent No.: US 11,771,590 B2
(45) Date of Patent: Oct. 3, 2023

(54) MEDICAL FLUID PROBE WITH HEAT SPREADER STRUCTURE AND THERMAL ENERGY SOURCE

(71) Applicant: Raytheon Company, Waltham, MA (US)

(72) Inventors: Samuel T. Craig, Tucson, AZ (US); Scott D. Nielsen, Sahuarita, AZ (US)

(73) Assignee: Raytheon Company, Waltham, MA (US)

( * ) Notice: Subject to any disclaimer, the term of this patent is extended or adjusted under 35 U.S.C. 154(b) by 529 days.

(21) Appl. No.: 16/871,557

(22) Filed: May 11, 2020

(65) Prior Publication Data

US 2021/0346193 A1 Nov. 11, 2021

(51) Int. Cl.
*A61F 7/12* (2006.01)
*A61M 5/44* (2006.01)
*A61F 7/00* (2006.01)
*A61B 10/00* (2006.01)

(52) U.S. Cl.
CPC .............. *A61F 7/12* (2013.01); *A61B 10/00* (2013.01); *A61F 2007/0054* (2013.01); *A61F 2007/0056* (2013.01); *A61F 2007/126* (2013.01); *A61M 5/44* (2013.01)

(58) Field of Classification Search
CPC .............. A61F 7/12; A61F 2007/0054; A61F 2007/0056; A61F 2007/126; A61B 10/00; A61B 2018/00005; A61B 2018/00023; A61B 18/08; A61M 5/44
See application file for complete search history.

(56) References Cited

U.S. PATENT DOCUMENTS

| | | | |
|---|---|---|---|
| 2,706,408 A | 4/1955 | Holbrook | |
| 4,275,603 A | 6/1981 | Kalocsay | |
| 4,578,061 A * | 3/1986 | Lemelson | A61N 5/1002 604/170.01 |
| 2015/0359976 A1 * | 12/2015 | Richards | A61M 5/44 604/113 |
| 2017/0029125 A1 | 2/2017 | Sarno | |
| 2019/0293676 A1 | 9/2019 | Jacobs et al. | |
| 2021/0349119 A1 | 11/2021 | Nielsen et al. | |

FOREIGN PATENT DOCUMENTS

| | | | | |
|---|---|---|---|---|
| CN | 104968290 B | * | 3/2018 | .............. A61B 18/02 |
| JP | S5912507 A | | 7/1984 | |

* cited by examiner

*Primary Examiner* — Carl H Layno
*Assistant Examiner* — Aya Ziad Bakkar
(74) *Attorney, Agent, or Firm* — Renner, Otto, Boisselle & Sklar

(57) ABSTRACT

A medical fluid probe includes a heat spreader structure that defines therein a fluid chamber that is in fluid communication with an external environment around the probe, and a thermal energy source in thermal communication with the heat spreader structure. The heat spreader structure functions as both temperature-control elements and structural elements. A variety of separate structure elements, such as the heat pipes, may combine to form the heat spreader structure. The thermal energy source may be used to maintain the temperature of the heat spreader structure, such as by heating and/or cooling the heater spreader structure.

17 Claims, 4 Drawing Sheets

MEDICAL FLUID PROBE WITH HEAT SPREADER STRUCTURE AND THERMAL ENERGY SOURCE

FIELD OF THE INVENTION

The invention is in the field of medical fluid probes.

DESCRIPTION OF THE RELATED ART

Medical fluid probes of various sorts are used to introduce and withdraw fluids or other materials from a body. Examples are in hypodermics and intravenous needles for introducing materials into a body, and biopsy needles for withdrawing material from a body.

SUMMARY OF THE INVENTION

In some circumstances it may be advantageous to control the temperature and/or the heating of a medical fluid probe (or of a fluid that passes through the probe) that is inserted into a patient. For example it may cause less discomfort or less disruption for a fluid probe to be maintained at a predetermined temperature, such as at a temperature close to that of the patient's body. As another example it may be advantageous for material, such as a medication, to be inserted into the patient's body at a controlled temperature. As still another example, it may be advantageous for material, such as a body fluid or biopsy sample, to be heated, cooled, or maintained at a given temperature while being removed from the patient's body.

In a general embodiment, a medical fluid probe includes a heat spreader structure configured to be inserted into a body of a patient, and a thermal energy source in thermal communication with the heat spreader structure. The thermal energy source may be used to heat, cool, and/or maintain the temperature of the heat spreader structure and fluid therein.

According to an aspect of the invention, a temperature-controlled medical probe including: a heat spreader structure that defines a fluid chamber therein, wherein a tip of the heat spreader structure is configured to be inserted into a patient, such that the fluid chamber is able to interact with the interior of the patient, to receive a sample from the patient and/or to inject a fluid into the patient; and a thermal energy source in thermal communication with the heat spreader structure; wherein the thermal energy source transfers heat between the heat spreader structure and the thermal energy source.

According to an embodiment of any paragraph(s) of this summary, the thermal energy source heats the heat spreader structure.

According to an embodiment of any paragraph(s) of this summary, the medical fluid probe is operatively connected to a fluid reservoir configured to provide a heated fluid to be injected into the patent.

According to an embodiment of any paragraph(s) of this summary, the thermal energy source cools the heat spreader structure.

According to an embodiment of any paragraph(s) of this summary, the medical fluid probe is operatively coupled to a fluid reservoir that is configured to provide a cryogenic fluid to be injected into the patient.

According to an embodiment of any paragraph(s) of this summary, the heat spreader structure is capable of being heated to enable heating of tissues of the patient.

According to an embodiment of any paragraph(s) of this summary, the heat spreader structure includes heat pipes.

According to an embodiment of any paragraph(s) of this summary, the heat pipes are attached together.

According to an embodiment of any paragraph(s) of this summary, the heat spreader elements are arrayed around a periphery of the medical probe.

According to an embodiment of any paragraph(s) of this summary, the probe further including a central heat spreader element surrounded by the heat spreader elements arrayed around the periphery of the fluid probe.

According to an embodiment of any paragraph(s) of this summary, the fluid chamber includes interstitial spaces between the central heat spreader element and the heat spreader elements.

According to an embodiment of any paragraph(s) of this summary, the heat spreader structure is at a tip of the medical probe.

According to an embodiment of any paragraph(s) of this summary, wherein the probe part of a system for injecting fluid into a patient, wherein the thermal energy source heats heated fluid to be injected into the patient.

According to an embodiment of any paragraph(s) of this summary, the system further including a fluid reservoir operatively coupled to the thermal energy source, the fluid reservoir containing the heated fluid to be injected into the patient.

According to an embodiment of any paragraph(s) of this summary, the system recirculates the fluid through the heated fluid through the patient.

According to an embodiment of any paragraph(s) of this summary, the system further including a pump that pumps the heated fluid from the fluid reservoir.

According to another aspect of the invention, a method of treating a patient using a medical probe including: inserting a heat spreader structure of the medical probe into a patient, wherein the defines a fluid chamber therein; heating and/or cooling the heat spreader structure using a thermal energy source of the medical probe that is in thermal communication with the heat spreader structure; and receiving a sample from the patient into the fluid chamber, and/or injecting a fluid into the patient from the fluid chamber.

According to an embodiment of any paragraph(s) of this summary, the method includes receiving the sample.

According to an embodiment of any paragraph(s) of this summary, the method includes injecting the fluid into the patient.

According to an embodiment of any paragraph(s) of this summary, the method further including pumping the fluid from a fluid reservoir.

According to an embodiment of any paragraph(s) of this summary, the fluid is heated by the thermal energy source, through the heat spreader structure, between the fluid reservoir and the patient.

To the accomplishment of the foregoing and related ends, the invention comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF DRAWINGS

The annexed drawings, which are not necessarily to scale, show various aspects of the invention.

DETAILED DESCRIPTION

Figure 1:
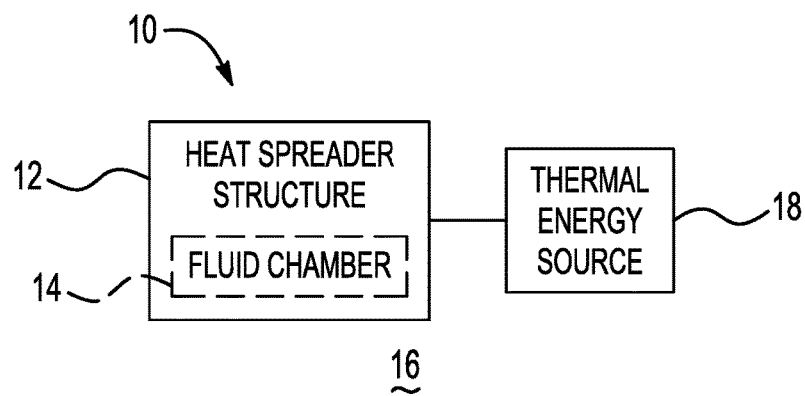
FIG. 1 is a block diagram of a fluid probe according to an embodiment of the invention.

In a general embodiment, a medical fluid probe includes a heat spreader structure that defines therein a fluid chamber that is in fluid communication with an external environment around the probe, and a thermal energy source in thermal communication with the heat spreader structure. The heat spreader structure functions as both temperature-control elements and structural elements. A variety of separate structure elements, such as the heat pipes, may combine to form the heat spreader structure. The thermal energy source may be used to maintain the temperature of the heat spreader structure, such as by heating and/or cooling the heater spreader structure.

This may help maintain the temperature of the fluid within the fluid chamber. More broadly, the thermal communication (or coupling) of the heat spreader structure and the thermal energy source may be used to transfer heat between the two, heating, cooling, and/or maintaining temperature of the heat spreader structure. The fluid probe may also include a tube that surrounds the fluid chamber, may further have one or more additional chambers in fluidic communication with the external environment.

When used as a means of sampling, or transferring or injecting a liquid, the heat spreader structure that defines the fluid chamber of heat pipes enables precision thermoregulation of the fluid probe and therefore also of the fluid within the fluid chamber. Additionally, an ability to maintain an isothermal temperature profile along the heat spreader structure enables the user to avoid disturbance of a sample, and/or to affect the temperature of a transferred liquid. Further, the heat spreader structure may be used to heat a liquid prior to injection into a patient.

Possible uses for the medical probe include large volume resuscitations, when pre-warmed liquid is transferred to the patient. A heat spreader structure could be used to construct the fluid passage that is the liquid transfer device. In that capacity, the tube structure could be heated to provide a fluid boundary that is maintained at the optimal liquid temperature along the length of the transfer tubing.

In large volume rapid transfusions, the liquid is warmed as it passes through tubing en route to the patient, which is currently accomplished using hot water wraps around the tubing. The probe could be used as the tubing device and coupled to a heating source to provide the means of warming the liquid, and would enable greater heating efficiency (more rapid heating of the liquid and over shorter distances) as well as greater precision in the temperature control.

Another use for the medical probe would be as a sampling device that enables improved quality of diagnostic testing for collected samples that degrade rapidly outside of a narrow temperature range, based on the extreme isothermal nature of the invention.

Additional potential uses for the medical probe include directed cryotherapy or directed tissue heating such as for tumor ablation. In the latter, the tumor tissue is heated to increase the metabolic activity and thus chemotherapeutic drug uptake by tumor cells. The medical probe could provide the means of application of heat to the tissue, whilst also providing the device through which the drug is injected. This would afford minimal probe diameters and hence minimal invasiveness of the foreign instrument. More generally, the medical probe device could be used in any application in which an optimal temperature exists at which to deliver drugs to maximize uptake.

FIG. 1 shows a block diagram of a temperature-controlled medical probe (or fluid probe) 10. The medical probe 10 includes a heat spreader structure 12 that at least in part defines within a fluid chamber 14 that is in fluid communication with an environment 16 external to the medical probe 10, such as inside a patient. The heat spreader structure 12 is thermally coupled to a thermal energy source 18. The thermal energy source 18 represents any of a variety of heaters, coolers, or thermal reservoirs, which may be used to transfer heat to and/or from the structure 12. The thermal energy source 18 may be used to maintain or control the temperature of the heat spreader structure 12, and/or to maintain or control the temperature of the fluid in the fluid chamber 14 via transfer of heat to/from the fluid by the heat spreader structure.

The heat spreader structure 12 is made up of elements that serve both as structural elements, in supporting the structure of the medical probe 10, and in allowing transmission of heat therethrough. One example of such an element is a heat pipe, which is a device with a working fluid therein, that uses thermal conductivity and phase change to transfer heat in a cycle between opposite ends of the heat pipe. A heat pipe has a wicking material around inner edges of a casing. In a cycling internal process within the heat pipe, the working fluid flows in liquid form along the wicking material by means of capillary forces, from a cold end of the heat pipe, which acts as a condenser, to the heat pipe's hot end, which acts as an evaporator. At the hot end the working fluid is heated to become gaseous vapor. The working fluid as a gas flow from the heat pipe's hot end to its cold end, along a central cavity or core that is free of the wicking material, due to the higher vapor pressure in the evaporator versus the condenser. At the cold end the gaseous working material cools and condenses again at the wicking material, starting the flow cycle over again. Heat pipes may have, for example, an effective thermal conductivity of from 10,000 W/m/K to 40,000 W/m/K. The heat transfer of the heat pipe may be used to maintain temperature, or otherwise transfer heat, in a medical probe. The heat pipe casing may be made of a suitable alloy that is compatible with the human body (or other body into which it is to be inserted). The heat pipes may be hermetically sealed to prevent leakage of the working fluid. The heat pipe (and the entire device) may be configured to be capable of sterilization by any of a variety of suitable processes, without incurring damage to functionality.

Heat pipes are not the only possible elements for the heat spreader structure 12. One alternative is a solid material with high thermal conductivity, for example annealed pyrolytic graphite or graphene. Broadly speaking, the heat spreader structure may be composed of heat transfer elements with a thermal conductivity of from 1,000 W/m/K to 10,000 W/m/K or to 40,000 W/m/K, to give nonlimiting ranges.

The term "structural element" is used herein to indicate a part that provides and/or maintains shape and/or rigidity of the part of the probe 10 that interacts with the environment in fluidic communication with the fluid chamber 14. In providing shape and/or rigidity the structural elements, either individually or collectively, may provide the majority of rigidity of the structure of that part of the fluid probe, for example maintaining the structural integrity (shape and/or rigidity) of a free-standing tip portion of the fluid probe. Looked at another way, the structural elements may provide essential structural support to the probe 10, or the part of the probe 10 that interacts with the environment, such that removal of some, most, and/or all of the structural elements may leave the probe 10 structural deficient for performing its intended purpose, whatever that purpose may be. For example, the heat spreader structure 12 may be used to maintain the shape of a free or distal end of the fluid probe (a tip of the fluid probe), where the probe interacts with the environment. Alternatively or in addition, the heat spreader structure 12 may make up the majority of the weight, volume, and/or structural strength of the portion of the fluid probe 10 (such as the tip) in which the heat spreader structure 12 is located.

The heat spreader structure 12 may constitute the outer walls of a portion of the fluid probe 10, for example constituting all of part of the outer walls of a free end or tip of the fluid probe 10. Alternatively or in addition, the heat spreader structure 12, in conjunction with the thermal energy source 18, may constitute a thermal barrier between the outer environment 16 and the fluid chamber 14.

Figure 2:
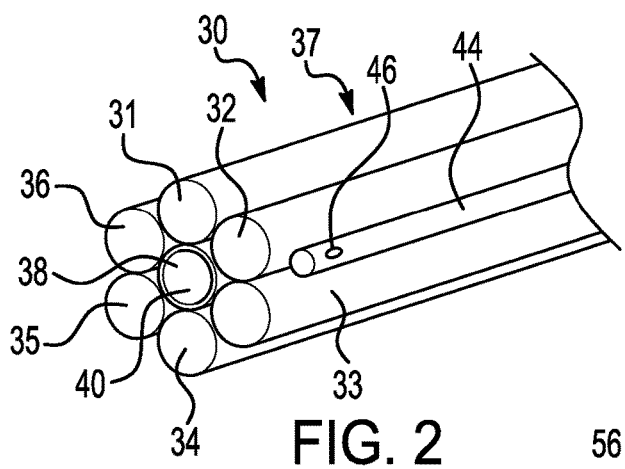
FIG. 2 is an oblique view of a fluid probe according to a second embodiment of the invention.

FIG. 2 shows a fluid probe 30, one embodiment of the medical probe. The fluid probe 30 includes six heat pipes 31, 32, 33, 34, 35, and 36, arranged in a hexagonal pattern to form a heat spreader structure 37 around a central tube or sampling tube 38. The central tube 38 is a hollow tube that surrounds a fluid chamber 40 therein that is open at its distal end. An optional additional tube 44 may be positioned toward the side, with a hole 46 possibly provided in the tube 44, such as for injecting and/or removing fluid. The heat pipes 31-36 may be operably (thermally) coupled to a heater or temperature source (a thermal energy source), for example to heat the probe 30, to cool the probe 30, and/or to control temperature in the probe 30.

Sampling tubes such as the central tube 38 may be used for any of a variety of reasons, such as introducing or removing fluids from a patient, and/or taking tissue or another medical sample from a patient. The central tube 38 may be made of a different material from that of the heat pipes 31-36, a material selected for compatibility with the environment around the probe 30 (such as an interior of a patient's body), or of a fluid or sample that may otherwise be in or pass through fluid chamber 40. The term "sampling tube" should be construed broadly as referring to a tube of whatever cross-sectional shape, that encloses and contacts a fluid chamber for receiving fluid or having fluid pass through, for any of a variety of purposes, some of which may involve operations beyond sampling, such as for injecting or otherwise introducing a fluid into a surrounding environment for any of a variety of purposes, such as for medical injection of fluids.

Whether or not the central tube 38 is present or is omitted, the heat spreader structure 37 defines at least in part the fluid chamber 40. Where the central tube 38 is omitted the heat spreader structure 37 directly defines the shape and volume of the fluid chamber 40. Even when the central tube 38 is present the heat spreader structure 37 at least partially defines the fluid chamber 40, at least by maintaining the shape and configuration of the central tube 38, even if there is no direct contact between the fluid within the chamber 40, and the heat pipes 31-36 of the heat spreader structure 37.

Figure 3:
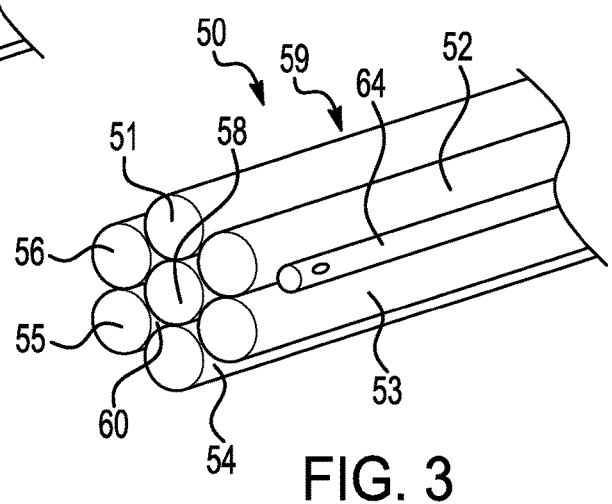
FIG. 3 is an oblique view of a fluid probe according to a third embodiment of the invention.

FIG. 3 shows a variation, a medical probe 50 similar to the medical probe 30 (FIG. 2), but with the central tube 38 (FIG. 2) replaced by a heat pipe 58, surrounded by six other heat pipes 51, 52, 53, 54, 55, and 56, arranged in a hexagonal pattern around the central heat pipe 58. The heat pipes 51-56 and 58 together constitute a heat spreader (heat pipe) structure 59. In such a configuration the volume within one or more of the interstitial openings 60 constitutes the fluid chamber of the probe 50. An additional tube 64, similar to the additional tube 44 (FIG. 2), may be part of the probe 50, such as for injecting and/or removing fluids, and/or for removing a tissue sample. As with the probe 30, the heat pipes 51-56 and 58 may be thermally coupled to a heater or temperature reservoir, for heating, cooling, or otherwise controlling temperature.

Figure 4:
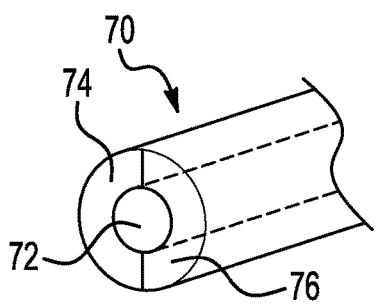
FIG. 4 is an end view of a fluid probe according to a fourth embodiment of the invention.
Figure 5:
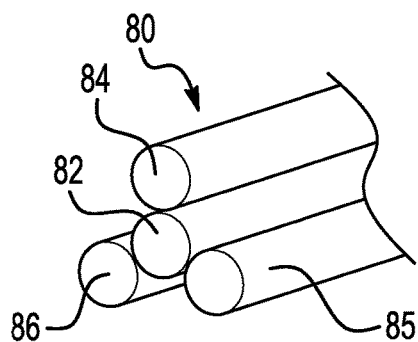
FIG. 5 is an end view of a fluid probe according to a fifth embodiment of the invention.
Figure 6:
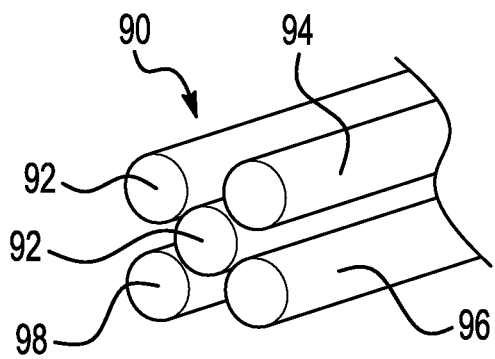
FIG. 6 is an end view of a fluid probe according to a sixth embodiment of the invention.
Figure 7:
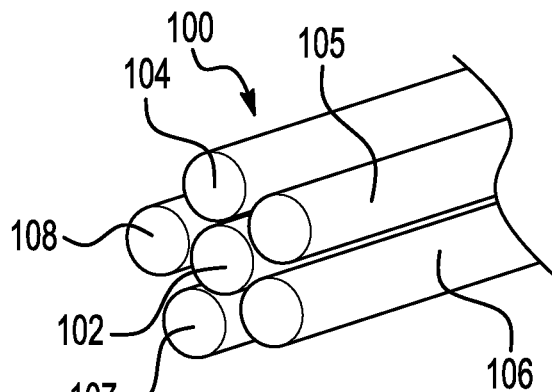
FIG. 7 is an end view of a fluid probe according to a seventh embodiment of the invention.

Many variations are possible for the arrangement of structural heat spreaders such as the heat pipes shown as structural parts of the medical probe 30 (FIG. 2) and the medical probe 50 (FIG. 3). FIG. 4 shows a medical probe 70 that includes a sampling tube 72 surrounded by a pair of semi-annular heat spreaders 74 and 76, for example suitably-shaped heat pipes. FIG. 5 shows a medical probe 80 with a central sampling tube 82 surrounded by three heat spreaders (such as heat pipes) 84, 85, and 86. FIG. 6 shows a medical probe 90 with a central sampling tube 92 surrounded by four heat spreaders (such as heat pipes) 94, 95, 96, and 97. FIG. 7 shows a medical probe 100 with a central sampling tube 102 surrounded by five heat spreaders (such as heat pipes) 104, 105, 106, 107, and 108.

Figure 8:
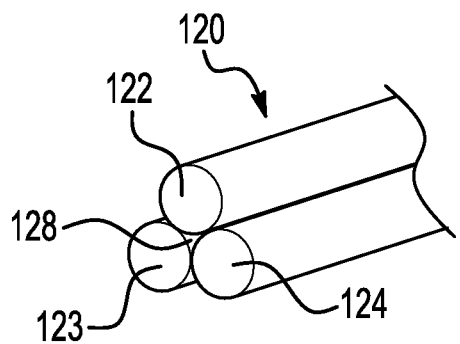
FIG. 8 is an end view of a fluid probe according to an eighth embodiment of the invention.
Figure 9:
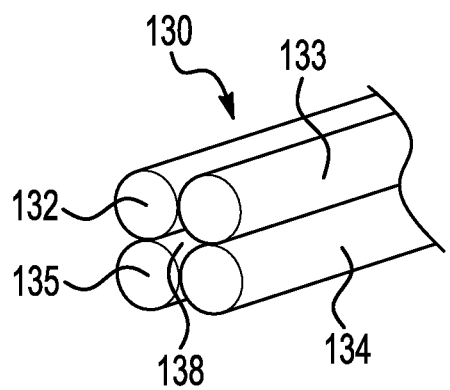
FIG. 9 is an end view of a fluid probe according to a ninth embodiment of the invention.
Figure 10:
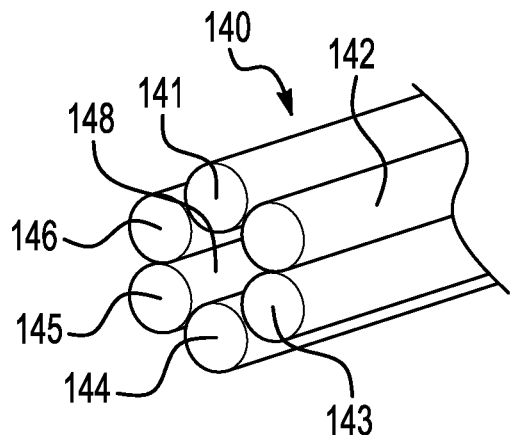
FIG. 10 is an end view of a fluid probe according to a tenth embodiment of the invention.

Relatedly, a variety of configurations may be used for a probe that relies on one or more interstitial spaces for use as a fluid chamber. FIG. 8 shows a medical probe 120 with three heat spreaders (or heat pipes) 122, 123, and 124 around an interstitial fluid chamber or space 128. FIG. 9 shows a fluid probe 130 with four heat spreaders (or heat pipes) 132, 133, 134, and 135 around an interstitial fluid chamber or space 138. FIG. 10 shows a medical probe 140 with six heat spreaders (or heat pipes) 141, 142, 143, 144, 145, and 146, around an interstitial fluid chamber or space 148.

Many configurations of the medical probe are also possible that use additional sampling tubes, akin to the additional tube 44 (FIG. 2) and the additional tube 64 (FIG. 3). Such additional tubes may provide additional fluid chambers in fluid communication with the surrounding environment (such as inside the body of a patient), or parts of the surrounding environment, for any of a variety of purposes, such as fluid sampling of parts of the environment or for injecting a fluid into different parts of the surrounding environment (and/or for injecting different fluids). The purposes given above for the additional tubes are intended to be non-limiting examples as opposed to an exhaustive list, and it should be appreciated that different combinations of uses of and/or purposes for various fluid chambers may be combined in a single probe or device.

Figure 11:
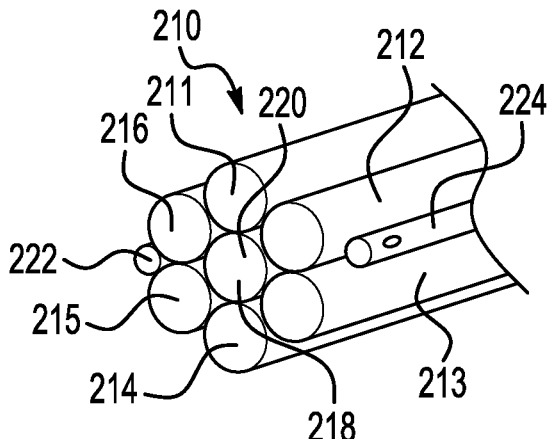
FIG. 11 is an end view of a fluid probe according to an eleventh embodiment of the invention.
Figure 12:
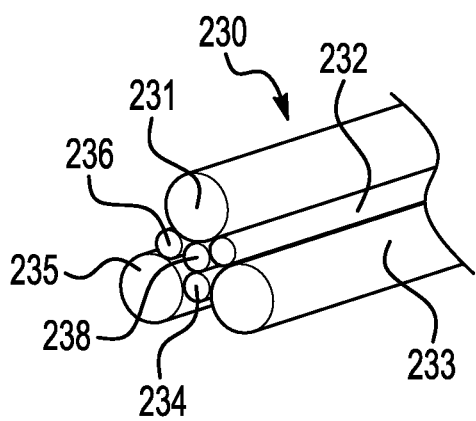
FIG. 12 is an end view of a fluid probe according to a twelfth embodiment of the invention.
Figure 13:
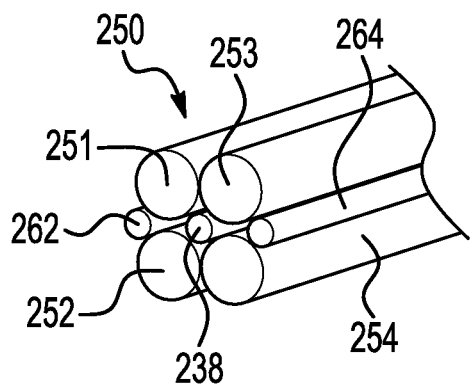
FIG. 13 is an end view of a fluid probe according to a thirteenth embodiment of the invention.
Figure 14:
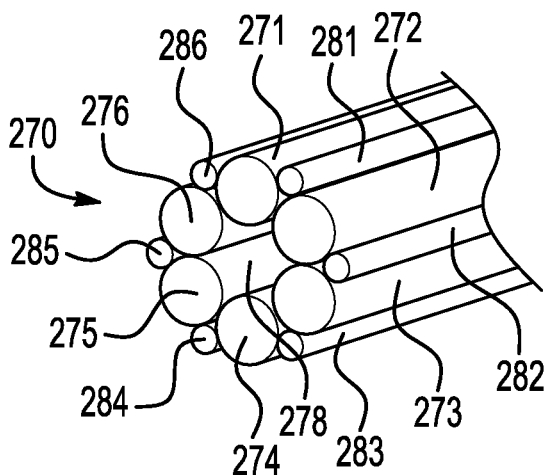
FIG. 14 is an end view of a fluid probe according to a fourteenth embodiment of the invention.

FIG. 11 shows a variant of the medical probe 30 (FIG. 2), a medical probe 210 that has six heat spreaders (or heat pipes) 211, 212, 213, 214, 215, and 216, in a hexagonal pattern surrounding a central tube 218 that defines a fluid chamber 220 therein. The medical probe 210 also includes a pair of additional tubes 222 and 224, which are on the perimeter of the fluid probe 210 and which are in fluid communication with different parts of the environment surrounding the fluid probe 210. FIG. 12 shows a medical probe 230 that includes a central tube 238 surrounded by alternating heat spreaders (or heat pipes) 231, 233, and 235, and secondary tubes 232, 234, and 236. FIG. 13 shows a medical probe 250 that includes four heat spreaders 251, 252, 253, and 254 around a central tube 258, with a pair of additional tubes 262 and 264. The additional tubes 262 and 264 are along the perimeter of the fluid probe 250, with the additional tube 262 in contact with the heat spreaders 251 and 252, and with the additional tube 264 in contact with the heat spreaders 253 and 254. FIG. 14 shows a further embodiment, a medical probe 270 which has heat spreaders 271, 272, 273, 274, 275, and 276 around a central fluid chamber 278, with an equal number of additional tubes 281, 282, 283, 284, 285, and 286 each contacting a pair of the heat spreaders 271-276.

Figure 15:
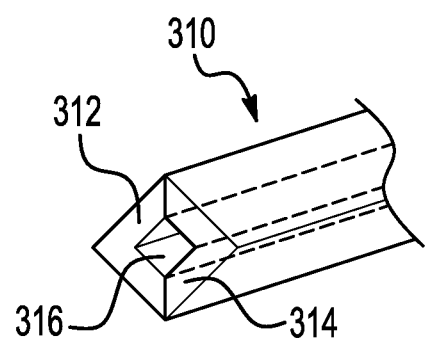
FIG. 15 is an end view of a fluid probe according to a fifteenth embodiment of the invention.
Figure 16:
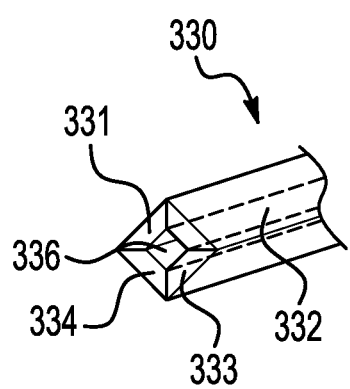
FIG. 16 is an end view of a fluid probe according to a sixteenth embodiment of the invention.
Figure 17:
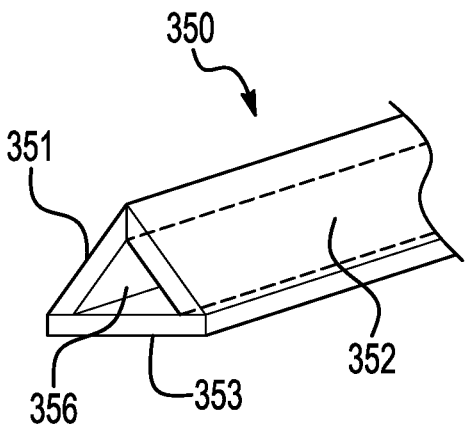
FIG. 17 is an end view of a fluid probe according to a seventeenth embodiment of the invention.

The heat spreaders, whether they are heat pipes or other materials, may have shapes other than round cross-section tubes. FIG. 15 shows a medical probe 310 that has a pair of angled heat spreaders 312 and 314 that together constitute a square cross-section end of the probe 310, and which together define within a square cross-section fluid chamber 316. FIG. 16 shows a variant, a medical probe 330 that has four heat spreaders 331, 332, 333, and 334. The heat spreaders 331-334 together constitute a square cross-section end of the probe 330, and which together define within a square cross-section fluid chamber 336. FIG. 17 shows another variant, a medical probe 350 that has three heat spreaders 351, 352, and 353, which together constitute a triangular cross-section end of the probe 350, and which together define within a triangular cross-section fluid chamber 356.

Figure 18:
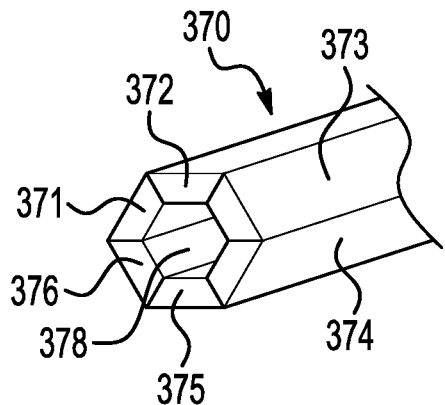
FIG. 18 is an end view of a fluid probe according to an eighteenth embodiment of the invention.
Figure 19:
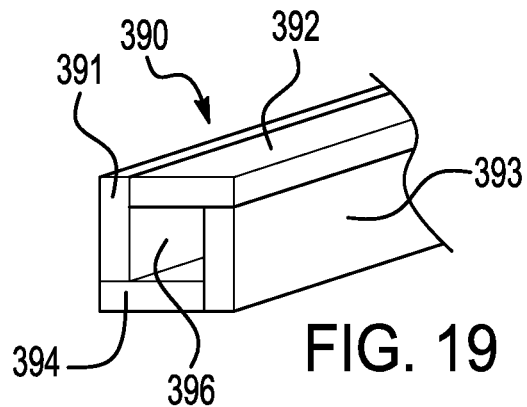
FIG. 19 is an end view of a fluid probe according to a nineteenth embodiment of the invention.

FIGS. 18 and 19 show further variants with polygonal probe cross-sectional areas, and corresponding polygonal cross-sections for fluid chambers. FIG. 18 shows a hexagonal medical probe 370 formed from six heat spreaders 371, 372, 373, 374, 375, and 376, defining a hexagonal cross-section fluid chamber 378. FIG. 19 shows a probe 390 that has a square cross-section made up of heat spreaders 391, 392, 393, and 394, joined together at lapped ends, and together defining a square cross-section fluid chamber 396.

It will be appreciated that many other polygonal cross-sections for the probe are possible. In addition it should be understood that such polygonal cross-sections may be regular or irregular polygons, and/or may be convex or concave, and/or that the fluid chamber and the surrounding parts of the probe (in particular the surrounding heat spreaders) may have different shapes. Further it will be appreciated other shapes are possible, such as combination of curved and straight sections.

The various features of the many embodiments shown in FIGS. 2-19 may be combined in a single embodiment, with different features drawn from different individual embodiments, in any suitable combination. Furthermore, features explained regarding one embodiment also may be applied to other embodiments, for example with a heater or temperature reservoir (or other heating, cooling, and/or temperature-stabilization device) being thermally coupled to heat spreaders of a fluid probe.

The heat spreaders in the various embodiments may be joined to each other and to other parts (such as tubes that define fluid chambers) by any of a variety of suitable methods or means of attachment. Examples include welding, brazing, and soldering, and adhesively attaching, for example by use of suitable epoxy or other adhesives. Another example is mechanical binding with a wrapping, such as a shrink sleeve or composite winding.

The thermal energy source coupled to the heat spreader structure of the fluid probes described herein can take any of a variety of forms. The thermal energy source can be (or can include) a heater, such as an electrical resistive heater; a cooler, such as a thermoelectric cooler; a device for maintaining temperature and/or transferring heat, such as a heat exchanger; or a thermal reservoir, such as a heat sink. Thermal energy sources are not illustrated in FIGS. 2-19, but it will be appreciated that all of the configurations of heat spreader structure in these embodiments are thermally coupled to (or may be thermally coupled to) a thermal energy source, for example any of the various sources described in this paragraph.

Figure 20:
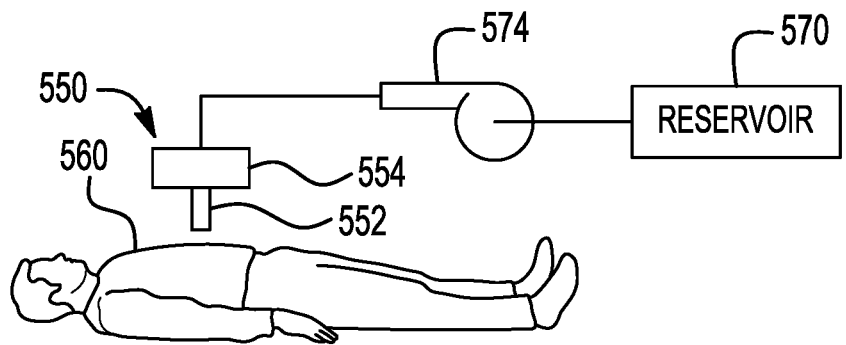
FIG. 20 shows use of a fluid probe as a medical device, according to another embodiment of the invention.

FIG. 20 illustrates a general use for medical probes such as those in the various embodiments described above. FIG. 20 shows a medical device probe 550 that includes a controlled-heat (or controlled-temperature) heat spreader structure 552 that is thermally coupled to a thermal energy source 554. The probe 550 may be inserted into a patient 560 to inject a fluid and/or to remove a sample, such as a sample fluid or a biopsy sample. It will be appreciated that it may be desirable to control temperature of the probe in such uses, for example to more closely match the temperature of the patient, such as for patient comfort or to avoid disruption to the body, and/or otherwise to provide a temperature suitable for the fluid or sample introduction or removal.

Optionally, there may be a fluid reservoir 570 that provides fluid to the medical probe 550, and specifically to the heat spreader structure 552. The fluid may be heated as it passed through the heat spreader structure 552 on the way from the fluid reservoir 570 to the patient 560, being indirectly heated by the thermal energy source 554. A pump 574 may be used to drive the fluid from the reservoir 570 to the heat spreader structure 552, and into the patient 560. The movement of the fluid may be a unidirectional introduction of the fluid into the patient 560, or may be part of a fluid recirculation through the patient 560, for example to warm the patient 560.

Figure 21:
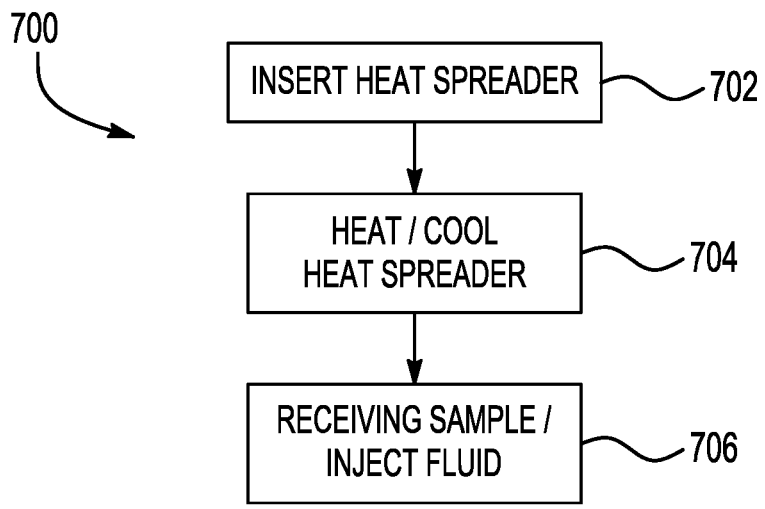
FIG. 21 is a high-level flow chart of a method of maintaining a thermal condition of a fluid probe, according to an embodiment of the invention.

FIG. 21 shows a high-level flowchart of a method 700 of use of a medical probe, such as those described above in various embodiments. In step 702 the heat spreader is inserted into the patient. In step 704 the heat spreader structure is heated and/or cooled using a thermal energy source of the medical probe that is in thermal communication. In step 706 a sample is received from the patient into the fluid chamber, and/or a fluid is injected into the patient from the fluid chamber.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A medical probe comprising:
    a heat spreader structure that defines a fluid chamber therein, wherein a tip of the heat spreader structure is configured to be inserted into a patient, such that the fluid chamber is able to interact with an interior of the patient, to receive a sample from the patient and/or to inject a fluid into the patient; and
    a thermal energy source in thermal communication with the heat spreader structure;
    wherein the thermal energy source transfers heat between the heat spreader structure and the thermal energy source; and
    wherein the heat spreader structure includes heat pipes arrayed around a periphery of a distal end of the medical probe, with the heat pipes configured to be inserted into the patient.

2. The medical probe of claim 1, wherein the thermal energy source heats the heat spreader structure.

3. The medical probe of claim 2, wherein the medical probe is operatively connected to a fluid reservoir configured to provide a heated fluid to be injected into the patient.

4. The medical probe of claim 1, wherein the thermal energy source cools the heat spreader structure.

5. The medical probe of claim 4, wherein the medical probe is operatively coupled to a fluid reservoir that is configured to provide a cryogenic fluid to be injected into the patient.

6. The medical probe of claim 1, wherein the heat spreader structure is capable of being heated to enable heating of tissues of the patient.

7. The medical probe of claim 1, wherein the heat pipes are attached together.

8. The medical probe of claim 1,
    further comprising a central heat spreader element surrounded by the heat pipes arrayed around the periphery of the medical probe; and
    wherein the fluid chamber includes interstitial spaces between the central heat spreader element and the heat pipes.

9. The medical probe of claim 1, as part of a system for injecting fluid into a patient, wherein the thermal energy source heats heated fluid to be injected into the patient, with the heated fluid indirectly heated by the thermal energy source, through the heat spreader structure.

10. The medical probe of claim 9, the system further comprising a fluid reservoir operatively coupled to the thermal energy source, the fluid reservoir containing the heated fluid to be injected into the patient.

11. The medical probe of claim 10, wherein the system recirculates the fluid through the heated fluid through the patient.

12. The medical probe of claim 10, the system further comprising a pump that pumps the heated fluid from the fluid reservoir.

13. A medical probe comprising:
    a heat spreader structure that defines a fluid chamber therein, wherein a tip of the heat spreader structure is configured to be inserted into a patient, such that the fluid chamber is able to interact with an interior of the patient, to receive a sample from the patient and/or to inject a fluid into the patient; and
    a thermal energy source in thermal communication with the heat spreader structure;
    wherein the thermal energy source transfers heat between the heat spreader structure and the thermal energy source;
    wherein the heat spreader structure includes a central heat pipe surrounded by peripheral heat pipes; and
    wherein the fluid chamber includes interstitial spaces between the central heat pipe and the peripheral heat pipes.

14. A method of treating a patient using a medical probe, the method comprising:
    inserting a heat spreader structure of the medical probe into a patient, wherein the heat spreader structure defines a fluid chamber therein, wherein the heat spreader structure includes heat pipes arrayed around a periphery of a distal end of the medical probe, with the heat pipes configured to be inserted into the patient;
    heating and/or cooling the heat spreader structure using a thermal energy source of the medical probe that is in thermal communication with the heat spreader structure; and
    receiving a sample from the patient into the fluid chamber, and/or injecting a fluid into the patient from the fluid chamber.

15. The method of claim 14, wherein the method includes receiving the sample.

16. The method of claim 14, wherein the method includes injecting the fluid into the patient.

17. The method of claim 16,
    further comprising pumping the fluid from a fluid reservoir;
    wherein the fluid is heated by the thermal energy source, through the heat spreader structure, between the fluid reservoir and the patient.

* * * * *